United States Patent [19]

Costantini et al.

[11] 4,092,361

[45] May 30, 1978

[54] PROCESS FOR THE PREPARATION OF 3,5,5-TRIMETHYL-CYCLOHEX-2-ENE-1,4-DIONE

[75] Inventors: Michel Costantini, Lyon; Adrien Dromard, Paris; Michel Jouffret, Francheville le Bas, all of France

[73] Assignee: Rhone-Poulenc Industries, Paris, France

[21] Appl. No.: 751,159

[22] Filed: Dec. 16, 1976

[30] Foreign Application Priority Data

Dec. 19, 1975 France .................................. 75 39783

[51] Int. Cl.$^2$ ............................................. C07C 45/00
[52] U.S. Cl. .................................................. 260/586 P
[58] Field of Search ..................................... 260/586 P

[56] References Cited

U.S. PATENT DOCUMENTS

| T900,015 | 7/1972 | Thweatt | 260/621 |
|---|---|---|---|
| 3,354,220 | 11/1967 | Brackman et al. | 260/586 P |
| 3,923,898 | 12/1975 | Schult-Elte | 260/586 R |
| 3,931,327 | 1/1976 | Stuckler et al. | 260/586 P |
| 3,944,620 | 3/1976 | Becker et al. | 260/586 P |
| 3,960,966 | 6/1976 | Widmer et al. | 260/586 P |
| 4,010,205 | 3/1977 | Becker | 260/586 P |
| 4,026,947 | 5/1977 | Costantine et al. | 260/586 P |
| 4,026,948 | 5/1977 | Becker et al. | 260/586 P |
| 4,046,813 | 9/1977 | Brenner | 260/586 P |

OTHER PUBLICATIONS

J. C. Dawber, "Chem & Ind.," p. 973 (1964).
Marx et al., "Tetrahedron," 22, Suppl. 8, p. 1 (1966).

*Primary Examiner*—Norman Morgenstern
*Attorney, Agent, or Firm*—Bacon & Thomas

[57] ABSTRACT

3,5,5-Trimethyl-cyclohex-2-ene-1,4-dione is prepared by a liquid phase oxidation of β-isophorone using carbon black as catalyst in the presence of a base.

10 Claims, No Drawings

PROCESS FOR THE PREPARATION OF 3,5,5-TRIMETHYL-CYCLOHEX-2-ENE-1,4-DIONE

BACKGROUND OF THE INVENTION

1. Field of the Invention

The present invention relates to a process for the preparation of 3,5,5-trimethyl-cyclohex-2-ene-1,4-dione from β-isophorone (3,5,5-trimethyl-cyclohex-3-en-1-one).

This diketone is useful in that it can be aromatized to give trimethylhydroquinone, which is known as an important intermediate in the synthesis of vitamin E. The conversion of 3,5,5-trimethyl-cyclohex-2-ene-1,4-dione to trimethylhydroquinone can be carried out, according to the process described in German Patent application No. 2,149,159, by the action of an acylating agent in the presence of a protonic acid of pKa < 3, or of a Lewis acid, followed by hydrolysis of the resulting diester.

2. Description of the Prior Art

Various methods for the preparation of 3,5,5-trimethyl-cyclohex-2-ene-1,4-dione have been proposed, which start either from α-isophorone (3,5,5-trimethyl-cyclohex-2-en-1-one) or from β-isophorone, which is easily obtained by isomerization of α-isophorone, by subjecting the latter to a slow distillation in the presence of a sulphonic acid (see French Pat. No. 1,446,246). Thus, according to French Pat. No. 2,213,264, the oxidation of α-isophorone can be carried out by means of an alkali metal chromate or bichromate or chromium trioxide in a mixture of acetic acid and acetic anhydride. This process requires the use of a large excess of oxidizing agent relative to the starting ketone in order to obtain yields of about 50% based upon the α-isophorone starting material. Furthermore, the treatment described for isolating the diketone, which treatment consists of pouring the reaction mixture onto ice and then extracting the organic phase with ether, has proved laborious because of the presence of the acetic acid. It should furthermore be noted that the excess oxidizing agent is difficult to recover and that the handling and the use, for the oxidation, of solutions of chromium compounds, such as those mentioned above, in acetic acid/acetic anhydride mixtures, are operations which can present explosion hazards [see J. C. DAWBER, Chemistry and Industry, page 973 (1964)]. For these reasons, this process is difficult to adapt to an industrial scale.

Several processes for the preparation of 3,5,5- trimethyl-cyclohex-2-ene-1,4-dione by oxidation of β-isophorone have also been described. French Pat. No. 1,446,246 has proposed oxidizing this ketone with oxygen, working in an alcoholic medium in the presence of a copper-II salt, of pyridine and of a tertiary amine; however, the method has a disadvantage that it only gives the diketone in a poor yield, of the order of 30%.

The French Patent Application published under No. 2,253,730 has described a process for the oxidation of β-isophorone to 3,5,5-trimethyl-cyclohex-2-ene-1,4-dione by means of molecular oxygen or of a gas which contains molecular oxygen, such as air, in the presence of a catalyst consisting of a derivative (an oxide, salt or complex) of a transition metal, such as vanadium, chromium, copper, manganese, iron, cobalt or nickel, which derivative can be used by itself or deposited on the usual supports and especially on silica, charcoal, calcium or magnesium carbonate or bicarbonate, or diatomaceous earth. The best results are obtained in a homegeneous phase, that is to say where the catalyst used is a metal derivative which is soluble in the reaction mixture, such as the metal salts of carboxylic acids (acetates) or the acetylacetonates. However, even under these conditions, which are claimed to be the best, the yields remain mediocre because they do not exceed 55% relative to the β-isophorone subjected to the oxidation, in spite of reaction times which are so long that this process loses any industrial value.

It is also possible to convert β-isophorone to 3,5,5-trimethyl-cyclohex-2-ene-1,4-dione indirectly, for example by treating the starting ketone with an organic peracid, then carrying out an alkaline hydrolysis of the resulting product, and thereafter oxidizing the 4-hydroxy-3,5,5-trimethyl-cyclohex-2-en-1-one formed in the preceding stage, by means of chromium trioxide. [see British Pat. No. 791,953 and J. N. MARX et al., Ietrahedron, 22, Suppl. 8, page 1 (1966)] The conversion of the β-isophorone to the diketone in this manner entails the use of several stages and the utilization of numerous reactants, which limits the industrial value of the process proposed.

In the final analysis, none of the above-mentioned processes lend themselves to the industrial production of 3,5,5-trimethyl-cyclohex-2-ene-1,4-dione and industry is still looking for a process which makes it possible to convert β-isophorone to this cyclohexenedione with, at one and the same time, good degress of conversion, good yields of diketone relative to the β-isophorone converted, and relatively short reaction times.

SUMMARY OF THE INVENTION

The object of the present invention resides primarily in a process wherein the advantages sought, as mentioned above, are realized.

More particularly, the present invention relates to a process for the preparation of 3,5,5-trimethyl-cyclohex-2-ene-1,4-dione by oxidation of β-isophorone in the liquid phase by means of molecular oxygen or of a gas containing it, in the presence of a base, characterized in that the reaction is carried out in the presence of carbon black as the catalyst.

DETAILED DESCRIPTION OF THE INVENTION

As the carbon black, it is possible to use charcoal of organic (vegetable or animal) origin or of mineral origin, such as those usually employed as catalyst supports, as agents for decolorizing organic liquids or aqueous solutions of various solutes, or as absorbents for gas purification. These different varieties of carbon black can optionally have been subjected to the usual activation treatments such as calcination or treatments with acids, steam or oxygen. The specific surface area of the carbon blacks used in the process of the invention can vary within wide limits; thus, it is possible to employ carbon blacks having a specific surface area of between 20 and 2,000 $m^2/g$ and preferably between 50 and 2,000 $m^2/g$. The particular mean size of the catalyst is not critical and it is equally possible to use fine powders and granules or fibers; the same is true of the porosity.

The amount of carbon black, expressed in terms of the weight of catalyst of 100 g of reaction mixture, can vary within wide limits; thus, it is possible to use from 0.001 to 20% by weight of catalyst relative to the weight of the reaction mixture. Preferably, amounts of carbon black representing from 0.5 to 20% by weight on this basis are used. The upper limit of 20% can be exceeded and still be within the scope of the present invention, but no appreciable advantage is achieved thereby.

The reaction temperature can vary quite extensively. In general, a temperature of between 0° and 100° C is suitable; however, temperatures ranging from 10° to 80° C and more particularly from 20° to 50° C are sufficient to give good yields of cyclohexenedione with relatively short reaction times.

The partial pressure of the oxygen used can be varied between 0.1 and 50 bars. Partial pressures of between 0.5 and 25 bars are quite suitable. As stated above, the molecular oxygen can be used by itself or in the form of its mixture with an inert gas, such as nitrogen or argon; for example, it is possible to use air, optionally enriched with, or depleted in, oxygen.

The base used to carry out the process according to the present invention can be an organic or inorganic base. Amongst the latter, there may be mentioned alkali metal hydroxide, e.g., sodium hydroxide or potassium hydroxide, and the alkali metal carbonates or alcoholates, e.g., sodium methylate or ethylate.

Organic bases which can be used include quaternary ammonium hydroxides, for example, tetramethylammonium hydroxide, trimethylhexylammonium hydroxide and trimethylbenzylammonium hydroxide or their salts derived from weak acids, for example, carbonates and acetates. Amines, polyamines and heterocyclic nitrogen-containing bases constitute a preferred class of bases suitable for carrying out the process according to the invention. Examples of such bases which may be mentioned are primary, secondary or tertiary aliphatic amines, particularly alkylamines, such as methylamine, ethylamine, propylamine, n-butylamine, isobutylamine, t-butylamine, the pentylamines, n-hexylamine, 2-ethylhexylamine, n-decylamine, dimethylamine, trimethylamine, diethylamine, triethylamine, di-isobutylamine, methyldiethylamine, methyldiisobutylamine, tri-n-propylamine, tri-n-butylamine; primary, secondary or tertiary cycloaliphatic amines, partiuclarly cycloalkylamines, such as cyclohexylamine, N-methylcyclohexylamine, N,N-diethylcyclohexylamine; aromatic amines such as aniline and diphenylamine, and araliphatic, particularly aralkyl, amines such as benzylamine or dibenzylamine. Amongst the heterocyclic bases which can be used, pyridine, piperidine or the N-alkylpiperidines may be mentioned. Although numerous amines and polyamines other than those mentioned above by way of non-limiting examples can be used, it is preferred to employ alkylamines in which the alkyl radical or radicals each contain from 1 to 8 carbon atoms and more preferably from 1 to 4 carbon atoms. Amongst the alkylamines, the secondary and tertiary amines are particularly suitable.

The amount of base employed can vary within wide limits. In general, at least 0.01 mol and preferably at least 0.1 mol of base is used per mol of β-isophorone. The maximum amount of base employed depends to a large extent on the nature of the base. It should be noted that if an amine is used as the base, it can constitute the reaction medium, so that strictly speaking there is no real upper limit to the value of the molar ratio of base/β-isophorone in this case. The value of this ratio thus essentially depends on practical considerations. Where the reaction is carried out in the presence of an inorganic solvent, it is not necessary for the molar ratio of base/ isophorone to have a value greater than 10; in general, an amount of base such that the upper limit of this ratio does not exceed 4 is sufficient.

The reaction can be carried out in the absence of a solvent or in the presence of an inert organic solvent. In the latter case, it is possible to employ an aliphatic hydrocarbon (pentane, hexane or heptane), a cycloaliphatic hydrocarbon (cyclohexane), an aromatic hydrocarbon (benzene, toluene and xylenes) or halogenated hydrocarbons (chloroform, dichloroethanes and chlorobenzene), alcohols (ethanol, isopropanol and t-butanol), ethers such as the glycol ethers (1,2-dimethoxyethane or diglyme), dioxane and tetrahydrofurane, ketones such as acetone, cyclohexanone, β-isophorone and 3,5,5-trimethyl-cyclohex-2-ene-1,4-dione, or, as has already been indicated, an organic base and in particular an amine. The use of α-isophorone as the reaction solvent is particularly advantageous because it makes it possible to employ mixtures of α- and β-isophorone such as those obtained from the partial isomerization of α-isophorone. The concentration of β-isophorone in the solvent employed is not critical and is determined in each instance so as to ensure the highest possible productivity of the reaction.

The desired end product, 3,3,5-trimethyl-cyclohex-2-ene-1,4-dione, may be recovered from the reaction mixture by a conventional technique. In practice, the carbon black can be separated from the reaction mixture by simply filtration and then recycled to a new oxidation operation; the filtrate can subsequently be distilled or be subjected to steam stripping in order to isolate the trimethylcyclohexenedione. The unconverted β-isophorone can, where appropriate, be re-used. The process according to the invention is particularly suitable for continuous operation.

The following examples are set forth as illustrative of the invention but not as limiting the same.

EXAMPLE 1

3.5 g of β-isophorone of 96.3% strength by weight, 25 cm$^3$ of acetone and 1.4 cm$^3$ of triethylamine are introduced into a 100 cm$^3$ three-neck flask equipped with a stirring system, a thermometer and a gas inlet connected to an oxygen supply.

The apparatus is flushed with a stream of oxygen and 0.9 g of active carbon black sold under the tradename "SPHERON 6" and having a specific surface area, measured by the nitrogen absorption method, of 103 m$^2$/g, are then introduced. The contents of the flask are kept at 20° C with stirring, under an atmosphere of pure oxygen; the volume of oxygen absorbed is followed as a function of time. After 3 hours 15 minutes, it is found that 87% of the theoretical volume of oxygen has been absorbed. The reaction mixture is filtered to remove the carbon black.

The products present in the filtrate are identified and determined by gas-liquid chromatography; the following results are obtained:

| | |
|---|---|
| unconverted β-isophorone: | 0.51 g, representing a degree of conversion of 84.9% |
| α-isophorone: | 0.07 g |
| 3,5,5-trimethyl-cyclohex-2-ene-1,4-dione: | 2.7 g, representing a yield of 85.3% relative to the β-isophorone converted |
| 3,5,5-trimethyl-4-hydroxy-cyclohex-2-en-1-one: | 0.15 g. |

EXAMPLE 2

3.5 g of β-isophorone of 96.3% purity by weight, 25 cm³ of acetone and 1 g of triethylamine are introduced into the apparatus described in Example 1, and the process described in that Example is then followed, replacing the "SPHERON-6" carbon black by 0.9 g of active carbon black, tradename "ACTICARBONE 2 S" having a specific surface area of 1,100 m²/g and a particle size of 60-100μ, with 55% of the pores having a diameter less than or equal to 13 A. After reaction for 2 hours 10 minutes, the theoretical volume of oxygen has been absorbed. After separating off the active charcoal by filtration, and washing three times with 15 cm³ of acetone, the following are determined in the filtrate:

unconverted β-isophorone: nil (degree of conversion: 100%)
trimethylcyclohexenedione: 2.2 g (yield 75.5%)

The preceding experiment is repeated, reusing the active charcoal recovered at the end of the reaction; the β-isophorone is completely converted and 2.77 g of the cyclohexenedione are determined, corresponding to a yield of 74%.

We claim:

1. In a process for the preparation of 3,5,5-trimethylcyclohex-2-ene-1,4-dione by oxidation of β-isophorone in the liquid phase by means of molecular oxygen or of a gas which contains molecular oxygen, the improvement consisting of carrying out said oxidation using carbon black as catalyst in the presence of a base.

2. A process according to claim 1, wherein the carbon black has a specific surface area of between 20 and 2,000 m²/g.

3. A process according to claim 1, wherein the amount of carbon black present is from 0.001 to 20% by weight of the reaction mixture.

4. A process according to claim 1, wherein the base is selected from the group consisting of an alkali metal hydroxide, carbonate or alcoholate, a quaternary ammonium hydroxide, an amine and a heterocyclic nitrogen-containing base.

5. A process according to claim 4, wherein said base is an alkylamine in which each alkyl radical contains from 1 to 8 carbon atoms.

6. A process according to claim 5, wherein said alkylamine is secondary or tertiary.

7. A process according to claim 6, wherein the alkylamine is selected from the group consisting of trimethylamine, triethylamine, diethylamine, diisopropylamine and diisobutylamine.

8. A process according to claim 1, wherein the amount of base present, expressed in mols per mol of starting β-isophorone is at least 0.01.

9. A process according to claim 8, wherein the amount of base present, expressed in mols per mol of starting β-isophorone is at least 0.01.

10. A process according to claim 1, wherein the oxidation temperature is between 0° and 100° C and the partial pressure of oxygen is between 0.1 and 50 bars.

* * * * *